(12) United States Patent
Shinno et al.

(10) Patent No.: US 9,066,852 B2
(45) Date of Patent: Jun. 30, 2015

(54) DENTAL ADHESIVE PRIMER COMPOSITION

(75) Inventors: Kazuya Shinno, Kyoto (JP); Toshiyuki Nakatsuka, Kyoto (JP); Akihiro Nagafuji, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 528 days.

(21) Appl. No.: 12/227,641

(22) PCT Filed: May 24, 2006

(86) PCT No.: PCT/JP2006/310378
§ 371 (c)(1),
(2), (4) Date: Apr. 22, 2009

(87) PCT Pub. No.: WO2007/135742
PCT Pub. Date: Nov. 29, 2007

(65) Prior Publication Data
US 2009/0299006 A1 Dec. 3, 2009

(51) Int. Cl.
*C08K 5/53* (2006.01)
*A61K 6/00* (2006.01)

(52) U.S. Cl.
CPC .................................. *A61K 6/0023* (2013.01)

(58) Field of Classification Search
CPC ............................ A61K 6/0023; C08L 33/00
USPC ........................................................ 524/807
See application file for complete search history.

(56) References Cited

U.S. PATENT DOCUMENTS

| | | | | |
|---|---|---|---|---|
| 5,925,690 A * | 7/1999 | Fuchigami et al. | ........... | 523/118 |
| 6,583,197 B1 | 6/2003 | Kouro et al. | | |
| 6,900,251 B2 * | 5/2005 | Moszner et al. | ............... | 522/171 |
| 6,916,858 B2 * | 7/2005 | Kojima et al. | ................ | 523/118 |
| 7,129,281 B2 * | 10/2006 | Fujiwara | ........................ | 522/153 |
| 7,776,936 B2 * | 8/2010 | Tanaka et al. | ..................... | 522/79 |
| 7,879,924 B2 * | 2/2011 | Torii et al. | ...................... | 523/116 |
| 2003/0083398 A1 * | 5/2003 | Kawashima et al. | ......... | 523/115 |
| 2009/0048366 A1 * | 2/2009 | Torii et al. | ...................... | 523/116 |
| 2010/0010115 A1 * | 1/2010 | Kohro et al. | ................... | 523/116 |

FOREIGN PATENT DOCUMENTS

| | | | |
|---|---|---|---|
| CA | 2065472 | | 10/1993 |
| EP | 0 712 622 | | 5/1996 |
| JP | 3-294286 | | 12/1991 |
| JP | 4-8368 | | 1/1992 |
| JP | 8-319209 | | 12/1996 |
| JP | 2001-72523 | | 3/2001 |
| JP | 2003-12430 | | 1/2003 |
| JP | 2004-26838 | * | 1/2004 |
| JP | 2005-247820 | * | 9/2005 |

OTHER PUBLICATIONS

Englsih translation of JP2005-247820 (machine translation from JPO).*
Maleic acid MSDS. No author, Oct. 1997. Obtained from Inchem. org.*
Yourtee et al. J. Biomed. Mat. Res. vol. 57. Iss. 4, pp. 522-531. 2001.*
Lewis, Richard J. Sr. Hawleys' Condensed Chemical Dictionary, 15$^{th}$ Edition. © 2007. p. 1163 "solution, true".*
Definition of "solution". No Author, No Date. Obtained from http://www.thefreedictionary.com/solution on Jul. 24, 2014.*
International Search Report dated Aug. 22, 2006 in the International (PCT) Application PCT/JP2006/310378 of which the present application is the U.S. National Stage.
Kunio Ikemura et al., "Effect of 4-Acryloxyethyltrimellitic Acid in a Self-etching Primer on Bonding to Ground Dentin", Dental Materials Journal, vol. 15, No. 2, pp. 132-143, 1996.
English translation of PCT Written Opinion dated Dec. 24, 2008 in the International (PCT) Application PCT/JP2006/310378 of which the present application is the U.S. National Stage.

* cited by examiner

*Primary Examiner* — Mark Eashoo
*Assistant Examiner* — Michael A Salvitti
(74) *Attorney, Agent, or Firm* — Wenderoth, Lind & Ponack, L.L.P.

(57) ABSTRACT

The present invention relates to a dental adhesive primer composition for use in dental fields employed to bond dental materials, such as restoration materials, dental crown materials, prosthetic materials, esthetic materials, orthodontic materials, preventive materials, core build-up materials and root canal materials, to ceramics, metals, resins, composite resins, glass ionomer cements, and hard biotissues (enamel or dentin of natural tooth). The present invention also relates to a dental adhesive primer composition including a dental adhesive composition which can be used not only in combination with another adhesive composition but also alone.

2 Claims, No Drawings

DENTAL ADHESIVE PRIMER COMPOSITION

TECHNICAL FIELD

The present invention relates to a dental adhesive primer composition for use in the dental field employed to bond dental materials, such as restoration materials, dental crown materials, prosthetic materials, esthetic materials, orthodontic materials, preventive materials, core build-up materials and root canal materials, to ceramics, metals, resins, composite resins, glass ionomer cements, and hard biotissues (enamel or dentin of natural teeth). The present invention also relates to a dental adhesive primer composition including a dental adhesive composition which can be used not only in combination with another adhesive composition but also alone.

BACKGROUND ART

Since composite resins have remarkably improved long-term durability and mechanical characteristics and also have characteristics such as fluorine sustained-release and X-ray contrast radiographic properties, composite resins have recently been used for functional and esthetic recovery of tooth substances when deficiency in the tooth substances is caused by the onset of dental caries or when there is a breakage or detachment of a dental crown restoration. Application of these composite resins has expanded to tooth face coating materials, fissure sealants, orthodontic bonding materials, and resin core materials. However, since these composite resins themselves not only have no adhesion, but also have adhesion to ceramics and metals, it is essential to use various bonding materials in combination. It is required for the bonding material to have excellent adhesion to both enamel containing an inorganic component such as hydroxyapatite as a main component and dentin containing an organic component such as collagen as a main component, particularly to the tooth substances. It has recently required for the bonding material to firmly bond to ceramics, metals, resins, composite resins, and glass ionomer cement and to have durability on adhesion.

In a conventional bonding material, after subjecting tooth surfaces to a tooth surface treatment using a strong etching material such as phosphoric acid, the bonding material is applied to bond tooth substances with a composite resin. However, a method for the tooth surface treatment using an acid etching material had a drawback such as complicated operation steps in which the acid applied on the tooth surface must be sufficiently removed by washing with water and the tooth surface dried.

The bonding method using the acid etching material showed sufficient adhesion to enamel as a result of formation of a roughened surface through decalcification of the acid etching material, and macroscopic mechanical fitting based on sufficient penetration and curing of the bonding material. In contrast, since a spongy collagen fiber is exposed to dentin as a result of decalcification of the acid etching material, the bonding material did not sufficiently penetrate into a collagen fiber and it was difficult to obtain sufficient adhesion.

In order to obtain high adhesion to dentin, an acid tooth surface treating material has been proposed which replaces the phosphoric acid etching material. For example, Japanese Unexamined Patent Publication (Kokai) No. 62-33109 discloses a tooth surface treating material containing a sulfonic acid group-containing polymer; Japanese Unexamined Patent Publication (Kokai) No. 62-231652 discloses a tooth surface treating material containing a metal halide; Japanese Unexamined Patent Publication (Kokai) No. 63-279851 discloses a tooth surface treating material containing an amphoteric amino compound; Japanese Unexamined Patent Publication (Kokai) No. 1-279815 discloses a tooth surface treating material containing an organic carboxylic acid and a metal chloride; and Japanese Unexamined Patent Publication (Kokai) No. 5-163111 discloses a tooth surface treating material containing an organic carboxylic acid and an iron phosphate.

However, it was difficult to obtain sufficient adhesion to dentin even when these acid tooth surface treating materials are used.

Japanese Patent No. 2,865,794 specification discloses, as a polymerizable compound having an acid group, an adhesive composition containing (a) a (meth)acrylate ester derivative having a phosphonic acid group, which is represented by the general formula (I):

[Chemical Formula 1]

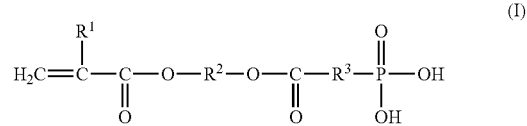

wherein $R^1$ represents a hydrogen atom or a methyl group, $R^2$ represents an alkylene group having 5 to 10 carbon atoms, and $R^3$ represents an alkylene group having 1 to 6 carbon atoms, (b) at least one kind of a radical polymerizable monomer, and (c) at least one kind of a polymerization initiator. When the phosphonic acid group contained in the (meth)acrylate ester derivative is applied on the dental substance, the phosphonic acid group is chemically bonded with a calcium component of the dental substance and, as a result, the phosphonic acid group can be imparted to the tooth surface. Although adhesion to enamel such as a resin cement can be improved by copolymerizing the polymerizable group with another polymerizable monomer in the resin cement, the resultant copolymer is not bonded to dentin at all.

Since it was presented that a primer is effective for penetration to a collagen fiber exposed by the acid tooth surface treating material applied on the tooth surface [Journal of Dental Research Vol. 63, P1087-1089, 1984: Primer Composition Comprising Glutaraldehyde/2-HEMA/Water], a three-step technique comprising acid treating agent/primer/bonding material has recently been used.

The proposed bonding method involving such a three-step technique includes methods described in Japanese Patent No. 3,399,573 and Japanese Patent No. 2,962,628.

Since 2-HEMA as a water-soluble polymerizable monomer contained in the primer stimulates mucous membranes, a primer composition containing another water-soluble polymerizable monomer to be replaced by 2-HEMA is also disclosed. For example, Japanese Unexamined Patent Publication (Kokai) No. 2004-137211 discloses a primer composition containing polyethylene glycol or polyethylene glycol monomethacrylate, and Japanese Patent No. 2,782,694 discloses a primer composition containing glyceryl mono (meth)acrylate.

However, these bonding techniques include a large number of complicated steps, and although they show high adhesion to enamel, they show insufficient adhesion to dentin.

An adhesive monomer having an acidic group in the molecule has recently been developed and there has been proposed a self-etching primer wherein a complicated operation step capable of simultaneously performing an acid treatment of decalcificating the tooth surface and a treatment of penetrating a primer into a collagen fiber is simplified. In the technique when the primer is used, an acid treatment to the tooth surface is not required and, after completion of a treatment (application/standing) of the tooth surface with the self-etching primer, a bonding material is applied after drying.

By treating the tooth surface, on which cavities are formed, with the self-etching primer, the self-etching primer penetrates into tooth substances (enamel/dentin) while dissolving a smear layer formed as a result of formation of cavities. After drying, the self-etching primer and the bonding material are integrated by applying the bonding material, followed by curing to obtain an adhesive layer.

A lot of proposals were made regarding the composition of these self-etching primers. For example, Japanese Unexamined Patent Publication (Kokai) No. 1-113057 discloses a primer composition comprising water/water-soluble film forming agent/salt of acid; Japanese Patent No. 2,634,276 discloses a primer composition comprising water/polymerizable compound having a hydroxyl group/polymerizable compound having an acid group/curing agent; Japanese Patent No. 3,480,654 and Japanese Patent No. 3,487,389 disclose dental primers comprising water/phosphoric acid group-containing polymerizable monomer/polyhydric carboxylic acid group-containing polymerizable monomer; Japanese Unexamined Patent Publication (Kokai) No. 7-82115 discloses a primer composition comprising vinyl compound having an acidic group/water-soluble vinyl compound having a hydroxyl group/water/aromatic sulfonate-aromatic amine; Japanese Unexamined Patent Publication (Kokai) No. 62-223289 discloses a primer composition comprising 2-HEMA/water containing an organic or inorganic acid; and Japanese Unexamined Patent Publication (Kokai) No. 4-8368 discloses a primer composition comprising water/polymerizable compound having an acid group/polymerizable compound having a hydroxyl group/amino compound having an acid group.

These compositions show a certain degree of adhesion to dentin, but do not show sufficient adhesion to enamel because they exert a poor decalcification action to an inorganic component.

Since the primer composition contains an acidic group-containing polymerizable monomer having poor polymerizability and a water-soluble polymerizable monomer, resulting in insufficient curing after application of the bonding material, and thus a problem such as poor durability on adhesion under a severe intraoral environment has occurred.

Furthermore, since these primer compositions are basically present in an acidic atmosphere where water and an acidic group-containing polymerizable monomer coexist, deterioration and change in quality are caused by hydrolysis of an intramolecular main chain and a functional group in components contained in the primer composition, and thus there were problems such as poor storage stability and material stability. Therefore, it was required to divide into a separate packaging form.

In order to solve these problems, there have been a lot of proposals regarding sufficiently curing an adhesive layer by using a primer and a bonding material in combination to thereby improve dental adhesion. For example, Japanese Unexamined Patent Publication (Kokai) No. 2000-212015 and Japanese Unexamined Patent Publication (Kokai) No. 2000-16911 disclose a dental adhesive system comprising a bonding material containing an acylphosphine oxide compound as a photopolymerization initiator, and a primer composition containing (polymerizable monomer having an acidic group/polymerizable monomer having a hydroxyl group/water); Japanese Unexamined Patent Publication (Kokai) No. 2004-26838 discloses a dental adhesion kit comprising a primer composition containing a phosphoric acid group-containing polymerizable monomer/water, and a bonding material containing a polyhydric carboxylic acid group-containing polymerizable monomer/polymerization initiator; Japanese Patent No. 3,236,030 discloses a novel bonding method using a bonding material comprising a primer solution containing a vinyl monomer having a specific molecular structure having a carboxyl group or an acid anhydride thereof, and an adhesive composition of a vinyl monomer having an acidic group; Japanese Unexamined Patent Publication (Kokai) No. 2000-204010 discloses a dental adhesion kit comprising a primer composition containing a sulfonic acid group-containing polymerizable monomer/water-soluble polymerizable monomer/water, and a bonding material containing an acidic phosphate ester-based polyfunctional polymerizable monomer; Japanese Unexamined Patent Publication (Kokai) No. 9-295313 discloses a dental adhesion kit comprising a primer composition containing sulfonic acid group-containing polymerizable monomer/water-soluble polymerizable monomer/water, and a bonding material containing a polyhydric carboxylic acid group-containing polyfunctional polymerizable monomer; Japanese Unexamined Patent Publication (Kokai) No. 11-180814 discloses a dental substance adhesive set comprising a self-etching primer containing acidic group-containing (meth)acrylate/water-soluble organic solvent/water, and a dental substance adhesive containing (meth)acrylate containing neither an acidic group nor a hydroxyl group/photopolymerization initiator/photopolymerization accelerator/filler; Japanese Unexamined Patent Publication (Kokai) No. 6-24928 discloses an adhesive comprising a primer solution composition containing specific metal compound/acidic group-containing polymerizable monomer/polymerizable monomer, and a curable composition containing trialkylboron or a partial oxide thereof as a polymerization catalyst; and Japanese Patent No. 3,449,755 discloses an adhesive kit comprising a primer composition containing acidic group-containing vinyl polymerizable compound/hydroxyl group-containing water-soluble vinyl compound/water/aromatic amine, and an acrylic adhesive containing acidic group-containing acrylic monomer/acidic group-noncontaining acrylic monomer/polymerization initiator.

All of these proposals enable realization of adhesion to tooth substances (enamel and dentin) by using in combination with a specific bonding material so as to improve curability of a primer composition containing an acidic group-containing polymerizable monomer having poor polymerizability and a water-soluble polymerizable monomer.

However, low curability involved in constituent components of the primer composition cannot be basically improved. Therefore, it is recognized that adhesion to both of enamel and dentin as well as durability on adhesion are insufficient.

Japanese Unexamined Patent Publication (Kokai) No. 10-251115 discloses, as a polymerizable compound having an acid group, a dental primer containing (A) a phosphoric acid group-containing polymerizable monomer having a —C—O—P ester bond, (B) a polyhydric carboxylic acid group-containing polymerizable monomer, and (C) water as main components.

According to this dental primer, a high adhesive strength of 20 MPa or more can be obtained in both dentin and enamel. However, an ester bond in the phosphoric acid group-containing polymerizable monomer used for this primer is likely to be hydrolyzed and is insufficient in storage stability and durability on adhesion.

[Patent Document 1]
  Japanese Unexamined Patent Publication (Kokai) No. 62-33109
[Patent Document 2]
  Japanese Unexamined Patent Publication (Kokai) No. 62-231652
[Patent Document 3]
  Japanese Unexamined Patent Publication (Kokai) No. 63-279851
[Patent Document 4]
  Japanese Unexamined Patent Publication (Kokai) No. 1-279815
[Patent Document 5]
  Japanese Unexamined Patent Publication (Kokai) No. 5-163111
[Patent Document 6]
  Japanese Patent No. 2,865,794 specification
[Patent Document 7]
  Japanese Patent No. 3,399,573
[Patent Document 8]
  Japanese Patent No. 2,962,628
[Patent Document 9]
  Japanese Unexamined Patent Publication (Kokai) No. 2004-137211
[Patent Document 10]
  Japanese Patent No. 2,782,694
[Patent Document 11]
  Japanese Unexamined Patent Publication (Kokai) No. 1-113057
[Patent Document 12]
  Japanese Patent No. 2,634,276
[Patent Document 13]
  Japanese Patent No. 3,480,654
[Patent Document 14]
  Japanese Patent No. 3,487,389
[Patent Document 15]
  Japanese Unexamined Patent Publication (Kokai) No. 7-82115
[Patent Document 16]
  Japanese Unexamined Patent Publication (Kokai) No. 62-223289
[Patent Document 17]
  Japanese Unexamined Patent Publication (Kokai) No. 4-8368
[Patent Document 18]
  Japanese Unexamined Patent Publication (Kokai) No. 2000-212015
[Patent Document 19]
  Japanese Unexamined Patent Publication (Kokai) No. 2000-16911
[Patent Document 20]
  Japanese Unexamined Patent Publication (Kokai) No. 2004-26838
[Patent Document 21]
  Japanese Patent No. 3,236,030
[Patent Document 22]
  Japanese Unexamined Patent Publication (Kokai) No. 2000-204010
[Patent Document 23]
  Japanese Unexamined Patent Publication (Kokai) No. 9-295913
[Patent Document 24]
  Japanese Unexamined Patent Publication (Kokai) No. 11-180814
[Patent Document 25]
  Japanese Unexamined Patent Publication (Kokai) No. 6-24928
[Patent Document 26]
  Japanese Patent No. 3,449,755
[Patent Document 27]
  Japanese Unexamined Patent Publication (Kokai) No. 10-251115
[Non-Patent Document 1]
  Journal of Dental Research Vol. 63, P 1087-1089, 1984

DISCLOSURE OF THE INVENTION

Thus, an object to be achieved by the present invention is to provide a dental adhesive primer composition which is sufficiently cured after removing a volatile component thereby making it possible to realize adhesion capable of firmly boding to enamel and dentin, and durability on adhesion capable of enduring even under the severe intraoral environment.

Another object to be achieved by the present invention is to provide a dental adhesive primer composition which enables a one-pack type packaging form having excellent storage stability in which deterioration and change in quality are less likely to be caused by hydrolysis of constituent components due to the environmental temperature or acidity of the solution.

The present inventors have intensively studied so as to achieve the above objects and found that, by using a phosphonic acid group-containing polymerizable monomer having at least one phosphonic acid group ($-PO(OH)_2$) or a phosphonic acid monoester group ($-PO(OH)(OR)$) bonded directly to a carbon atom and at least one polymerizable unsaturated group in the molecule in combination with a polyhydric carboxylic acid group-containing polymerizable monomer having at least two carboxylic acid groups or a group capable of easily reacting with water to form two or more carboxylic acid groups and at least one polymerizable unsaturated group in the molecule in the dental adhesive primer composition, the resultant dental adhesive primer composition can be firmly bonded to both of enamel and dentin and also has durability on adhesion capable of enduring even under the severe intraoral environment. Thus, the present invention has been completed.

The present inventors have also found that the dental adhesive primer composition obtained by using the phosphonic acid group-containing polymerizable monomer in combination with the polyhydric carboxylic acid group-containing polymerizable monomer has excellent storage stability in which deterioration and change in quality are less likely to be caused by hydrolysis of constituent components even under the acidic atmosphere. Thus, the present invention has proposed.

It is recognized that the dental adhesive primer composition of the present invention can be firmly bonded to both of enamel and dentin and also has durability on adhesion capable of enduring even under the severe intraoral environment by containing a combination of the phosphonic acid group-containing polymerizable monomer and the polyhydric carboxylic acid group-containing polymerizable monomer as adhesive monomers.

It is also recognized that the dental adhesive primer composition containing these adhesive monomers of the present invention has excellent storage stability even under the acidic atmosphere in the presence of water.

BEST MODE FOR CARRYING OUT THE INVENTION

The dental adhesive primer composition of the present invention comprises:
(a) a phosphonic acid group-containing polymerizable monomer;
(b) a polyhydric carboxylic acid group-containing polymerizable monomer;
(c) water;
(d) a water-soluble organic solvent; and
(e) a polymerization catalyst.

The phosphonic acid group-containing polymerizable monomer contained, as an essential component, in the dental adhesive primer composition of the present invention means a polymerizable monomer having at least one (—PO(OH)$_2$) bonded directly to a carbon atom, or a phosphonic acid monoester group (—PO(OH)(OR)) and at least one polymerizable unsaturated group in the molecule.

It is possible to use those having any functional group in the molecule without any limitation as long as these conditions are satisfied. In the phosphonic acid group-containing polymerizable monomer, the number of phosphonic acid groups or phosphonic acid monoester groups, and the kind and number of radical polymerizable unsaturated groups such as (meth)acryloyl groups, styryl groups, vinyl groups, and allyl groups in the molecule are not particularly limited.

The dental adhesive primer composition of the present invention can exhibit excellent dental adhesion performance to enamel when compared with the polymerizable monomer having a phosphoric acid monoester group or a phosphoric acid diester group by containing the phosphonic acid group-containing polymerizable monomer. The phosphonic acid group-containing polymerizable monomer is scarcely hydrolyzed in the molecule even under the acidic atmosphere in the presence of water and is excellent in storage stability since a phosphonic acid group is not bonded with an oxygen atom through an ester bond. Therefore, the packaging form may be not only a two-pack type packaging form divided into two sections, but also a one-pack type packaging form.

It is preferred to use, among these phosphonic acid group-containing polymerizable monomers, a phosphonic acid group-containing polymerizable monomer represented by the general formula (I):

[Chemical Formula 2]

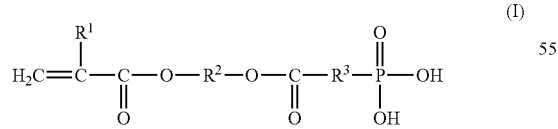

(I)

wherein $R^1$ represents a hydrogen atom or a methyl group, $R^2$ represents an alkylene group having 5 to 10 carbon atoms, and $R^3$ represents an alkylene group having 1 to 6 carbon atoms, which has excellent dental adhesion and storage stability.

Specific examples of the phosphonic acid group-containing polymerizable monomer represented by the general formula (I) include, but are not limited to, the following compounds.

[Chemical Formula 3]

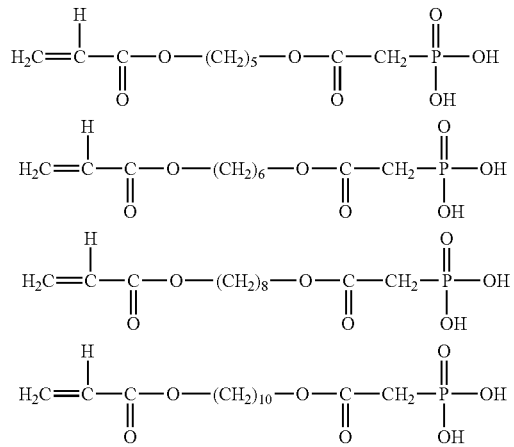

[Chemical Formula 4]

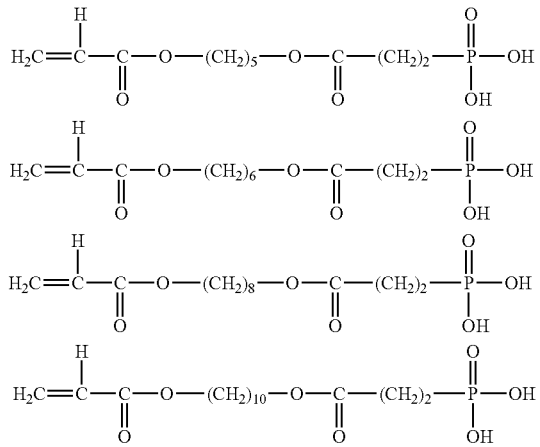

[Chemical Formula 5]

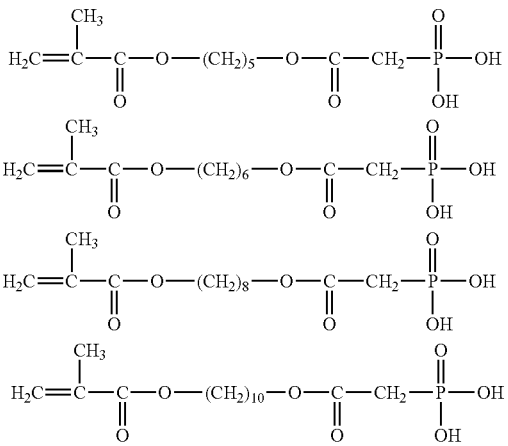

[Chemical Formula 6]

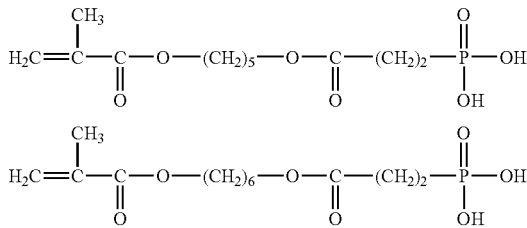

-continued

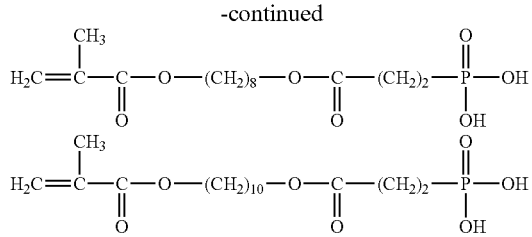

These phosphonic acid group-containing polymerizable monomers can also be used alone or in combination. It is more preferred to use, among phosphonic acid group-containing polymerizable monomers, 6-(meth)acryloyloxyhexyl phosphonoacetate, 6-(meth)acryloyloxyhexyl-3-phosphonopropionate, 10-(meth)acryloyloxydecyl-3-phosphonoacetate, 10-(meth)acryloyloxydecyl phosphonopropionate, and 5-(meth)acryloyloxypentyl-3-phosphonopropionate.

The content of these phosphonic acid group-containing polymerizable monomers can be appropriately selected according to the application or purpose and usage of the dental adhesive primer composition, and is preferably within a range from 0.1 to 40.0 parts by weight.

When the content of these phosphonic acid group-containing polymerizable monomers is more than 40.0 parts by weight, since curability involved in polymerizability deteriorates, an adverse influence is exerted on bond characteristics. In contrast, when the content of these phosphonic acid group-containing polymerizable monomers is less than 0.1 parts by weight, the effect is not recognized in adhesion to enamel.

The polyhydric carboxylic acid group-containing polymerizable monomer (b) contained, as an essential component, in the dental adhesive primer composition of the present invention means a polymerizable monomer having two or more carboxylic acid groups, or a group capable of easily reacting with water to form two or more carboxylic acid groups and at least one polymerizable unsaturated group in the molecule.

It is possible to use those having any functional group in the molecule without any limitation as long as these conditions are satisfied. In the polyhydric carboxylic acid group-containing polymerizable monomer, the kind and number of radical polymerizable unsaturated groups such as (meth)acryloyl groups, styryl groups, vinyl groups, and allyl groups in the molecule are not particularly limited. The dental adhesive primer composition of the present invention can exhibit excellent dental adhesion performance to dentin by containing the polyhydric carboxylic acid group-containing polymerizable monomer.

Specific examples of the polyhydric carboxylic acid group-containing polymerizable monomer include, but are not limited to, aconitic acid, measaconic acid, maleic acid, maleic anhydride, itaconic acid, itaconic anhydride, fumaric acid, glutaconic acid, citraconic acid, utraconic acid, 1,4-di(meth)acryloyloxyethylpyromellitic acid, 6-(meth)acryloyloxynaphthalene-1,2,6-tricarboxylic acid, 1-butene 1,2,4-tricarboxylic acid, 3-butene 1,2,3-tricarboxylic acid, 4-(meth)acryloyloxyethyltrimellitic acid and an anhydride thereof, 4-(meth)acryloyloxybutyltrimellitic acid and an anhydride thereof, β-(meth)acryloyloxyethyl hydrogen succinate, β-(meth)acryloyloxyethyl hydrogen maleate, 11-(meth)acryloyloxy-1,1-undecanedicarboxylic acid, 4-(meth)acryloyloxyethoxycarbonylphthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid and acid anhydride thereof, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, and 11-(meth)acryloyloxy-1,1-undecanedicarboxylic acid. These polyhydric carboxylic acid group-containing polymerizable monomers can also be used alone or in combination. It is more preferred to use, among these polyhydric carboxylic acid group-containing polymerizable monomers, 4-methacryloyloxyethyltrimellitic acid and an anhydride thereof, and 4-acryloyloxyethyltrimellitic acid and an anhydride thereof.

The content of these polyhydric carboxylic acid group-containing polymerizable monomers can be appropriately selected according to the application or purpose and usage of the dental adhesive primer composition, and is preferably within a range from 0.1 to 40.0 parts by weight.

When the content of these polyhydric carboxylic acid group-containing polymerizable monomers is more than 40.0 parts by weight, since curability involved in polymerizability deteriorates, an adverse influence is exerted on bond characteristics. In contrast, when the content of these polyhydric carboxylic acid group-containing polymerizable monomers is less than 0.1 parts by weight, the effect is not recognized in adhesion to dentin.

When adhesion to tooth substances is further enhanced in the dental adhesive primer composition of the present invention or adhesion to various adherends containing noble metal is imparted, the dental adhesive primer composition may contain an acidic group-containing polymerizable monomer other than the phosphonic acid group-containing polymerizable monomer and the polyhydric carboxylic acid group-containing polymerizable monomer, a polymerizable monomer containing a sulfur atom in the molecule and a silane compound alone, or in combination.

As long as the acidic group-containing polymerizable monomer other than the phosphonic acid group-containing polymerizable monomer and the polyhydric carboxylic acid group-containing polymerizable monomer has at least one acidic group in the molecule, the kind of an acidic group is not particularly limited and any acidic group-containing polymerizable monomer having an acidic group can be used.

Specific examples of the acidic group of the acidic group-containing polymerizable monomer include, but are not limited to, a phosphoric acid group (monoester or diester), a monocarboxylic acid group, a pyrophosphoric acid group, a sulfonic acid group, and a thiophosphoric acid group. Also there is no limitation on the number (monofunctional group or polyfunctional group) and the kind of the radical polymerizable unsaturated group of the polymerizable monomer having an acidic group.

Specific examples of the unsaturated group of the acidic group-containing polymerizable monomer include a (meth)acryloyl group, a styryl group, a vinyl group, and an allyl group. Among these unsaturated groups, an acidic group-containing polymerizable monomer having a (meth)acryloyl group is preferred. Furthermore, these acidic group-containing polymerizable monomers can also have another functional group such as alkyl groups, halogens, amino groups, glycidyl groups or hydroxyl groups in the molecule.

Specific examples of the acidic group-containing polymer having a (meth)acryloyl group as the unsaturated group include the followings.

Examples of the acidic group-containing polymerizable monomer having a phosphoric acid group include, but are not limited to, (meth)acryloyloxymethyl dihydrogen phosphate, 2-(meth)acryloyloxyethyl dihydrogen phosphate, 3-(meth)

acryloyloxypropyl dihydrogen phosphates 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, di(meth)acryloyloxyethyl hydrogen phosphate, di(meth)acryloyloxybutyl hydrogen phosphate, di(meth)acryloyloxyhexyl hydrogen phosphate, di(meth)acryloyloxyoctyl hydrogen phosphate, di(meth)acryloyloxynonyl hydrogen phosphate, di(meth)acryloyloxydecyl hydrogen phosphate, 1,3-di(meth)acryloyloxypropyl-2-dihydrogen phosphate, 2-(meth)acryloyloxyethylphenyl hydrogen phosphate, 2-(meth)acryloyloxyethyl 2'-bromoethyl hydrogen phosphate, and (meth)acryloyloxyethylphenyl phosphonate.

Examples of the acidic group-containing polymerizable monomer having a monocarboxylic acid group include, but are not limited to, (meth)acrylic acid, 2-chloro(meth)acrylic acid, 3-chloro(meth)acrylic acid, 2-cyano(meth)acrylic acid, N-(meth)acryloyl-p-aminobenzoic acid, N-(meth)acryloyl-5-aminosalicylic acid, 2-(meth)acryloyloxybenzoic acid, p-vinylbenzoic acid, and 5-(meth)acryloylaminopentylcarboxylic acid.

Examples of the acidic group-containing polymerizable monomer having a pyrophosphoric acid group include, but are not limited to, di[2-(meth)acryloyloxyethyl]pyrophosphate, di[3-(meth)acryloyloxypropyl]pyrophosphate, di[4-(meth)acryloyloxybutyl]pyrophosphate, di[5-(meth)acryloyloxypentyl]pyrophosphate, di[6-(meth)acryloyloxyhexyl]pyrophosphate, di[7-(meth)acryloyloxyheptyl]pyrophosphate, di[8-(meth)acryloyloxyoctyl]pyrophosphate, di[9-(meth)acryloyloxynonyl]pyrophosphate, di[10-(meth)acryloyloxydecyl]pyrophosphate, di[12-(meth)acryloyloxydodecyl]pyrophosphate, tetra[2-(meth)acryloyloxyethyl]pyrophosphate, and tri[2-(meth)acryloyloxyethyl]pyrophosphate.

Examples of the acidic group-containing polymerizable monomer having a sulfonic acid group include, but are not limited to, 2-(meth)acrylamide-2-methylpropanesulfonic acid, styrenesulfonic acid, 2-sulfoethyl(meth)acrylate, 4-(meth)acryloyloxybenzenesulfonic acid, and 3-(meth)acryloyloxypropanesulfonic acid.

Examples of the acidic group-containing polymerizable monomer having a thiophosphoric acid group include, but are not limited to, 10-(meth)acryloyloxydecyl dihydrogen dithiophosphate.

The acidic group-containing polymerizable monomers were described above but are not limited thereto, and polymerizable monomers having such an acidic group can also be used alone or in combination. Furthermore, not only an acidic group-containing polymerizable monomer having a short main chain, but also an oligomer, a prepolymer and a polymer, each having a long main chain, can be used without any limitation.

It is also possible to use derivatives of the acidic group-containing polymerizable monomer, such as a metal salt, ammonium salt or acid chloride in which the acidic group of the acidic group-containing polymerizable monomer is partially neutralized as long as an adverse influence is not exerted on adhesion to various adherends.

It is also effective for the present invention to use a polymerizable monomer containing a sulfur atom in the molecule so as to impart adhesion to noble metal to the dental adhesive primer composition of the present invention. The polymerizable monomer containing a sulfur atom in the molecule can be used regardless of the kind and number of unsaturated groups as well as the presence or absence of another functional group.

Specific examples of the polymerizable monomer having a (meth)acryloyl group as the unsaturated group which contains a sulfur atom in the molecule include, but are not limited to, (meth)acrylate having a triazinethiol group, (meth)acrylate having a mercapto group, (meth)acrylate having a polysulfide group, (meth)acrylate having a thiophosphoric acid group, (meth)acrylate having a disulfide cyclic group, (meth)acrylate having a mercaptodiathiazole group, and (meth)acrylate having a thiouracil group. These polymerizable monomers containing a sulfur atom in the molecule can also be used alone or in combination.

It is also effective for the present invention to use an organosilane compound having at least one polymerizable unsaturated group in the molecule so as to impart adhesion to a ceramic or composite resin to the dental adhesive primer composition of the present invention. The organosilane compound having a polymerizable unsaturated group in the molecule can be used regardless of the kind and number of unsaturated groups as well as the presence or absence of another functional group. Specific examples of the organosilane compound having a polymerizable unsaturated group include, but are not limited to, vinyltrimethoxysilane, vinyltriethoxysilane, vinyltrichlorosilane, vinyl(β-methoxyethoxy)silane, and γ-methacryloxypropyltrimethoxysilane. These organosilane compounds can also be used alone or in combination.

Water (c) contained, as an essential component, in the dental adhesive primer composition of the present invention has a function of activating an acidic group of the phosphonic acid group-containing polymerizable monomer and polyhydric carboxylic acid group-containing polymerizable monomer contained in the dental adhesive primer composition thereby promoting a decalcification action to tooth substances and promoting penetration into tooth substances. Therefore, water can be used without any limitation as long as it does not contain impurities which exert an adverse influence on storage stability, biocompatibility, polymerizable and dental adhesion. It is preferred to use distilled water or ion-exchange water.

The content of water can be appropriately selected according to the application or purpose and usage of the dental adhesive primer composition of the present invention, and is preferably within a range from 0.1 to 80.0 parts by weight. When the content of water is more than 80.0 parts by weight, it is impossible to maintain the composition at a homogeneous state and separation arises, and thus an adverse influence is exerted on storage stability. In contrast, when the content of water is less than 0.1 parts by weight, it is impossible to obtain sufficient adhesion to various adherends including tooth substances.

The water-soluble organic solvent (d) contained, as an essential component, in the dental adhesive primer composition of the present invention plays a role, which is similar to that of a dissolution accelerator, of compatibilizing various polymerizable monomers including the phosphonic acid group-containing polymerizable monomer and polyhydric carboxylic acid group-containing polymerizable monomer contained in the dental adhesive primer-composition, water, a polymerization catalyst and another component in an optional ratio, and also has a function of promoting penetration of the dental adhesive primer composition into tooth substances. Also the water-soluble organic solvent can decrease liquid viscosity of the dental adhesive primer composition thereby improving operability such as dropwise addition from a container, or application to the site to be bonded.

Specific examples of the water-soluble organic solvent include, but are not limited to, alcohols such as methanol, ethanol, 1-propanol, 2-propanol, and 1-butanol; ether compounds such as triethylene glycol monomethyl ether, triethylene glycol monomethyl ether, dipropylene glycol monomethyl ether, tetrahydrofuran, and dimethoxyethane; and ketone compounds such as acetone and methyl ethyl ketone. These water-soluble organic solvents can also be used alone or in combination. Among these water-soluble organic solvents, methanol, ethanol, 1-propanol, 2-propanol and acetone are preferred since they are excellent in compatibility with water, and acetone and ethanol are more preferred.

The content of the organic solvent can be appropriately selected according to the application or purpose and usage of the dental adhesive primer composition of the present invention, and is preferably within a range from 0.1 to 80.0 parts by weight. When the content of the organic solvent is more than 80.0 parts by weight, adhesion to tooth substances deteriorates. In contrast, when the content of the organic solvent is less than 0.1 parts by weight, it is impossible to maintain the composition at a homogeneous state and separation arises, and thus an adverse influence is exerted on storage stability.

The polymerization catalyst (e) contained, as an essential component, in the dental adhesive primer composition of the present invention is not particularly limited and a known radical generator can be used without any limitation. The polymerization catalyst is roughly classified into a catalyst capable of initiating polymerization by mixing immediately before use (chemical polymerization catalyst), a catalyst capable of initiating polymerization by heating or warming (thermal polymerization catalyst), and a catalyst capable of initiating polymerization by light irradiation (photopolymerization catalyst) and all of these catalysts can also be used alone or in combination.

Examples of the chemical polymerization catalyst include redox type polymerization catalysts comprising organic peroxide/amine compound, organic peroxide/amine compound/sulfinate, or organic peroxide/amine compound/borate compound; and polymerization catalysts capable of initiating polymerization by reacting with oxygen or water, such as organoboron compounds, perborates, permagnates, and persulfates. Furthermore, sulfinates, borate compounds and barbiturates are capable of initiating polymerization in the presence of water and/or a polymerizable monomer having an acidic group.

Specific examples of the organic peroxide include, but are not limited to, benzoyl peroxide, parachlorobenzoyl peroxide, 2,4-dichlorobenzoyl peroxide, acetyl peroxide, lauroyl peroxide, tertiary butyl peroxide, cumen hydroperoxide, 2,5-dimethylhexane, 2,5-dihydroperoxide methyl ethyl ketone peroxide, and tertiary butyl peroxybenzoate. These organic peroxides can also be used alone or in combination.

The amine compound is preferably a secondary or tertiary amine in which an amine group is bonded with an aryl group, and specific examples thereof include, but are not limited to, N,N-dimethyl-p-toluidine, N,N-dimethylaniline, N-β-hydroxyethyl-aniline, N,N-di(β-hydroxyethyl)-aniline, N,N-di(β-hydroxyethyl)-p-toluidine, N-methyl-aniline, and N-methyl-p-toluidine. These amine compounds can also be used alone or in combination.

Specific examples of the sulfinates include, but are not limited to, sodium benzenesulfinate, lithium benzenesulfinate, and sodium p-toluenesulfinate. These sulfinates can also be used alone or in combination.

Specific examples of the borate compound include, but are not limited to, sodium, lithium, potassium, magnesium, tetrabutylammonium and tetramethylammonium salts of trialkylphenylboron and trialkyl(p-fluorophenyl)boron (alkyl group represents an n-butyl group, an n-octyl group, or an n-dodecyl group). These borate compounds can also be used alone or in combination.

Specific examples of the barbituric acids include, but are not limited to, barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-barbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid and thiobarbituric acids, and salts thereof (alkali metal or alkali earth metals are particularly preferred). Examples of the salts thereof include, but are not limited to, sodium 5-butylbarbiturate, sodium 1,3,5-trimethylbarbiturate, calcium 1,3,5-trimethylbarbiturate, and sodium 1-cyclohexyl-5-ethylbarbiturate. These barbiturates can also be used alone or in combination.

When the dental adhesive primer composition of the present invention is used alone, these chemical polymerization catalysts must be separately contained in at least two packaging-forms. When the dental adhesive primer composition of the present invention is used together with another composition, both the dental adhesive primer composition of the present invention and another composition can contain the chemical polymerization catalyst so as to initiate chemical polymerization by bringing the dental adhesive primer composition into contact with another composition.

Among these chemical polymerization catalysts, sulfinates, barbiturates and organic peroxide-tertiary amine are preferably used alone or in combination, and organic peroxide-tertiary amine, organic peroxide-tertiary amine-barbiturates and organic peroxide-tertiary amine-sulfinates are more preferably used.

The content of the chemical polymerization catalyst is preferably within a range from 0 to 15.0 parts by weight, and more preferably from 0.1 to 10.0 parts by weight, based on 100 parts by weight of the dental adhesive primer composition.

Examples of the photopolymerization catalyst include those composed of only a photosensitizer and those composed of a combination of a photosensitizer and a photopolymerization accelerator.

The photosensitizer is roughly classified into those in which polymerization is initiated by ultraviolet rays and those in which polymerization is initiated by visible rays.

Specific examples of the photosensitizer which can be used as the photopolymerization catalyst include, but are not limited to, α-diketones such as benzyl, camphorquinone, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone, and naphthoquinone; benzoin alkyl ethers such as benzoin, benzoin methyl ether and benzoin ethyl ether; thioxanthones such as thioxanthone, 2-chlorothioxanthbne, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, acetoinbenzophenone, p-chlorobenzophenone, and p-methoxybenzophenone; acylphosphine oxides such as 2,4,6-trimethylbenzoyldiphenylphosphine oxide and bis(2,6-dimethoxybenzoyl)-2,4,4-trimethylpentylphosphine oxide; α-aminoacetophenones such as 2-benzyl-dimethylamino-1-(4-morpholinophenyl)-butanone-1 and 2-benzyl-diethylamino-1-(4-morpholinophenyl)-propanone-1; ketals such as benzyl dimethyl ketal, benzyl diethyl ketal and benzyl(2-methoxyethyl ketal); and titanocenes such as bis(cyclopentadienyl)-bis[2,6-difluoro-3-(1-pyrrolyl)phenyl]-titanium, bis(cyclopentadienyl)-bis(pentanefluorophenyl)-titanium, and bis(cyclopentadienyl)-bis(2,3,5,6-tetrafluoro-4-disiloxyphenyl)-titanium. These photosensitizers can also be used alone or in combination.

Specific examples of the photopolymerization accelerator which can be used as the photopolymerization catalyst include, but are not limited to, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, ethyl p-dimethylaminobenzoate, p-dimethylaminobenzoic acid amino ester, methyl N,N-dimethylanthranate, N,N-dihydroxyethylaniline, N,N-dihydroxyethyl-p-toluidine, p-dimethylaminophenyl alcohol, p-dimethylaminostyrene, N,N-dimethyl-3,5-xylidin, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)dimethanol; secondary amines such as N-phenylglycine; barbiturates such as 5-butylbarbituric acid, 1-benzyl-5-phenylbarbitur, 1,3,5-trimethylbarbituric acid, sodium 1,3,5-trimethylbarbiturate, and calcium 1,3,5-trimethylbarbiturate; tin compounds such as dibutyltin diacetate, dibutyltin dilaurate, dioctyltin dilaurate, dioctyltin diperacetate, dioctyltin bis(mercaptoacetic acid isooctyl ester) salt, and tetramethyl-1,3-diacetoxydistannoxane; aldehyde compounds such as laurylaldehyde and terephthalaldehyde; and sulfur-containing compounds such as dodecylmercaptan, 2-mercaptobenzooxazole, 1-decanethiol, and thiosalicylic acid. These photopolymerization accelerators can also be used alone or in combination.

It is effective to add, in addition to the above photopolymerization accelerator, citric acid, malic acid, tartaric acid, glycolic acid, gluconic acid, and oxycarboxylic acids such as α-oxyisobutyric acid, 2-hydroxypropanoic acid, 3-hydroxypropanoic acid, 3-hydroxybutanoic acid, 4-hydroxybutanoic acid and dimethylolpropionic acid so as to improve photopolymerization acceleration ability.

When the photopolymerization catalyst is used, one packaging form or a packaging form divided into two sections may be used without any limitation. Among these photopolymerization catalysts, a combination of α-diketone, a tertiary amine or α-diketone and tin compounds is preferred. More preferred is a combination of camphorquinone and an aromatic tertiary amine in which an amino group of ethyl p-N, N-dimethylaminobenzoate is directly bonded to the benzene ring or an aliphatic tertiary amine having a double bond in the molecule of N,N-dimethylaminoethyl methacrylate, or a combination of camphorquinone, dibutyltin dilaurate and tin compounds such as dioctyltin dilaurate. The content of the photopolymerization catalyst is preferably within a range from 0.1 to 15.0 parts by weight, more preferably from 0.1 to 10.0 parts by weight, and most preferably from 0.1 to 8.0 parts by weight, based on 100 parts by weight of the dental adhesive primer composition.

Examples of the thermal polymerization catalyst capable of initiating polymerization by heating or warming which can be used include, but are not limited to, azo compounds such as azobisisobutyronitrile and methyl azobisisobutyrate azobiscyanovaleric acid are preferably used, in addition to the above organic peroxide. These thermal polymerization catalysts can also be used alone or in combination.

According to the application, coumarin-based, cyanine-based and thiazine-based sensitizing dyes; photo acid generators which are irradiated with light to generate Brønsted acid or Lewis acids, such as a halomethyl group substituted-s-triazine derivative, diphenyliodonium salt compound, etc.; quaternary ammonium halides; and transition metal compounds can be appropriately used.

As the hydrophobic polymerizable monomer as the component (f) in the dental adhesive primer composition of the present invention, a monofunctional or polyfunctional polymerizable monomer which exhibits hydrophobicity can be used without any limitation, regardless of the kind of a radical polymerizable unsaturated group.

Examples of the radical polymerizable unsaturated group of the hydrophobic polymerizable monomer include (meth)acryloyl group, (meth)acrylamide group, styryl group, vinyl group, and allyl group. It is particularly preferred to use a hydrophobic polymerizable monomer having a (meth)acryloyl group or (meth)acrylamide group as an unsaturated group. The hydrophobic polymerizable monomer which exhibits hydrophobicity can also have another functional group such as halogen, amino group, glycidyl group and hydroxyl group in the molecule.

Regarding the "hydrophobic polymerizable monomer", a polymerizable monomer having solubility in 100 parts by weight of water at 23° C. of less than 10 parts by weight is defined as a hydrophobic polymerizable monomer. That is, when 10 g of a polymerizable monomer is added in 100 g of water maintained at 23° C. in a sample bottle, followed by stirring with mixing for 10 minutes and further standing, if the mixture is separated into phases in the sample bottle, the polymerizable monomer is defined as a hydrophobic polymerizable monomer.

Specific examples of the hydrophobic polymerizable monomer in which a radical polymerizable unsaturated group is a (meth)acryloyl group among the hydrophobic polymerizable monomer include monofunctional group-containing hydrophobic polymerizable monomer, for example, (meth)acrylate esters such as methyl (meth)acrylate, ethyl (meth)acrylate, butyl (meth)acrylate, hexyl (meth)acrylate, tetrahydrofurfuryl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, methoxypolyethylene glycol (meth)acrylate, and isobonyl (meth)acrylate; silane compounds such as γ-(meth)acryloyloxypropyltrimethoxysilane and γ-(meth)acryloyloxypropyltriethoxysilane; and nitrogen-containing compounds such as 2-(N,N-dimethylamino)ethyl (meth)acrylate.

Examples of the aromatic difunctional group-containing hydrophobic polymerizable monomer include 2,2-bis(4-(meth)acryloyloxyphenyl)propane, 2,2-bis(4-(3-(meth)acryloyloxy-2-hydroxypropoxy)phenyl) propane, 2,2-bis(4-(meth)acryloyloxyethoxyphenyl)propane, 2,2-bis(4-(meth)acryloyloxydiethoxyphenyl)propane, 2,2-bis(4-(meth)

acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2-(4-(meth) acryloyloxyethoxyphenyl)-2-(4-(meth) acryloyloxydiethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxydipropoxyphenyl)propane, and 2,2-bis(4-(meth) acryloyloxyisopropoxyphenyl)propane.

Examples of the aliphatic difunctional group-containing hydrophobic polymerizable monomer include ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol-di(meth)acrylate, 1,3-butanediol di(meth)acrylate, 1,4-butanediol di(meth)acrylate, 1,6-hexanediol di(meth)acrylate, and di-2-(meth)acryloyloxyethyl-2,2,4-trimethylhexamethylenedicarbamate.

Examples of the aliphatic trifunctional group-containing hydrophobic polymerizable monomer include trimethylolpropane tri(meth)acrylate, trimethylolethane tri(meth)acrylate, and trimethylolpropane tri(meth)acrylate.

Examples of the aliphatic tetrafunctional group-containing hydrophobic polymerizable monomer include pentaerythritol tetra(meth)acrylate and pentaerythritol tetraacrylate.

Specific examples of the urethane-based hydrophobic polymerizable monomer include di(meth)acrylates, which has a di- or tri-functional, or higher polyfunctional polymerizable group and also have an urethane bond, derived from adducts of polymerizable monomers having a hydroxyl group such as 2-hydroxyethyl (meth)acrylate, 2-hydroxypropyl (meth)acrylate and 3-chloro-2-hydroxypropyl (meth)acrylate, and diisocyanate compounds such as methylcyclohexane diisocyanate, methylenebis(4-cyclohexyl isocyanate), hexamethylene diisocyanate, trimethylhexamethylene diisocyanate, isophorone diisocyanate, diisocyanatemethylmethylbenzene and 4,4-diphenylmethane diisocyanate. As long as it has a meth)acrylate group, not only a monomer having a short main chain, but also an oligomer, a prepolymer and a polymer, each having a long main chain, can be used without any limitation.

These hydrophobic polymerizable monomers are not limited thereto and can also be used alone or in combination.

Among these hydrophobic polymerizable monomers, those having solubility in 100 parts by weight of water at 23° C. of less than 5 parts by weight is preferred, and those having solubility in 100 parts by weight of water at 23° C. of less than 1 part by weight is more preferred. Specifically, 2,2-bis(4-(3-methacryloyloxy-2-hydroxypropoxy)phenyl)propane (Bis-GMA), 2,2-bis(4-methacryloyloxyethoxyphenyl)propane (D-2.6E), di(methacryloyloxy)-2,2,4-trimethylhexamethylenediurethane (UDMA), triethylene glycol dimethacrylate (TEGDMA), neopentyl glycol dimethacrylate, and trimethylolpropane trimethacrylate are preferably used.

The content of the hydrophobic polymerizable monomer to be mixed with the dental adhesive primer composition is preferably within a range from 1.0 to 50.0 parts by weight, and more preferably from 1.0 to 30.0 parts by weight, based on 100 parts by weight of the total weight in the dental adhesive primer composition. When the content deviates from the above range, wettability to the surface of the adherend to be bonded deteriorates and curability involved in polymerizability deteriorates, and thus bond characteristics deteriorate.

A preferred aspect of the dental adhesive primer composition of the present invention is that it does not contain a hydrophilic polymerizable monomer which is easily compatible with water. The hydrophilic polymerizable monomer has the effect of compatibilizing a hydrophobic component contained in the dental adhesive primer composition with a hydrophilic component in an optional ratio, and enhancing adhesion by improving permeability and wettability to an interface to be bonded. However, since the dental adhesive primer composition is present under an acidic atmosphere, deterioration and change in quality of the hydrophilic polymerizable monomer are caused by hydrolysis, and thus adhesion may deteriorate. Furthermore, the hydrophilic polymerizable monomer originally has poor curability and causes hydrolysis when cured since it has high affinity with water, and thus a problem is recognized in durability on adhesion.

Regarding the "hydrophilic polymerizable monomer" as used herein, a polymerizable monomer having solubility in 100 parts by weight of water at 23° C. of 10 parts by weight or more is defined as a hydrophilic polymerizable monomer. That is, when 10 g of a polymerizable monomer is added in 100 g of water maintained at 23° C. in a sample bottle, followed by stirring with mixing for 10 minutes and further standing, if the mixture is compatible in a transparent or semitransparent state in the sample bottle, the polymerizable monomer is defined as a hydrophilic polymerizable monomer.

Specific examples of the hydrophilic polymerizable monomer in which a radical polymerizable unsaturated group is a (meth)acryloyl group among the hydrophilic polymerizable monomer include, but are not limited to, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammonium ethyl(meth)acrylchloride, (meth)acrylamide, 2-hydroxyethyl(meth)acrylamide, and polyethylene glycol di(meth)acrylate (those having 9 or more oxyethylene groups).

The dental adhesive primer composition preferably does not contain a hydrophilic polymerizable monomer having solubility in 100 parts by weight of water at 23° C. of 20 parts by weight or more, and more preferably a hydrophilic polymerizable monomer having solubility in 100 parts by weight of water at 23° C. of 40 parts by weight or more. Specific examples thereof include 2-hydroxyethyl (meth)acrylate, polyethylene glucol di(meth)acrylate (those having 9 or more oxyethylene groups), polyethylene glucol di(meth)acrylate (those having 14 oxyethylene groups), and polyethylene glucol di(meth)acrylate (those having 23 oxyethylene groups).

The dental adhesive primer composition can contain fillers for the purpose of improving operability by thickening the dental adhesive primer composition of the present invention or improving adhesion by imparting a mechanical strength to a bond interface layer. The filler is not particularly limited and fillers known as a dental filler can be used. Examples of the filler include inorganic filler and/or organic filler and/or organic-inorganic composite filler, and these fillers can be used alone or in combination.

The shape of these fillers maybe any shape such as a spherical shape, needle shape, tabular shape, ground shape or scaly shape and is not particularly limited. Furthermore, the diameter of these filler is not particularly limited, and is preferably within a range from 0.001 to 10 μm, and more preferably from 0.01 to 5 μm, in consideration of problems such as sedimentation and separation.

Among these fillers, AEROSIL, as ultrafine particles, produced by a vapor phase method, or silica-zirconia oxide particles, as ultrafine silica composite particles, produced from the solution of the sol-gel reaction are effective for the present invention since they function as a thickener when mixed in the dental adhesive primer composition. Specific examples of AEROSIL include AEROSIL 200, AEROSIL OX50, AEROSIL R972, AEROSIL R974, AEROSIL R8200, AEROSIL R711, AEROSIL DT4, Aluminum Oxide C, and Titanium Dioxide P25. Also cohesive inorganic fillers obtained by intended cohesion of the ultrafine particles may be used without causing any problems.

It is possible to optionally add components, for example, ultraviolet absorbers such as 2-hydroxy-4-methylbenzophenone; polymerization inhibitors such as hydroquinone, hydroquinone monomethyl ether, and 2,5-di-tertiary butyl-4-methylphenol; discoloration inhibitors; antibacterial agent; coloration pigment; and another conventionally known additive; in the dental adhesive primer composition.

The usage in the dental adhesive composition of the present invention is not particularly limited, and the dental adhesive composition can be used not only alone but also used appropriately in combination with another composition such as an etching material, primer, bonding material, self-etching primer, ceramic primer, metal primer, noble metal primer, etc.

The dental adhesive primer composition of the present invention has a feature that it is excellent in storage stability according to the constitution of components contained in the composition. Therefore, the dental adhesive primer composition can be formed into a one-pack packaging form. The dental adhesive primer composition of the present invention can also be formed into a two- or higher-pack packaging form according to the content of components, and the kind and usage of the polymerization catalyst, which can be appropriately selected.

EXAMPLES

The present invention will be described in detail by way of Examples and Comparative Examples, but the present invention is not limited to the following Examples.

Test methods for evaluation of performances of dental adhesive primer compositions prepared in the following Examples are as follows.

(1) Dental Adhesion Test
Evaluation Object:
Evaluation of dental adhesion to enamel and dentin using various dental adhesive primer compositions
Evaluation Procedure:
After thawing bovine lower jaw permanent central incisors which were withdrawn within 24 hours after slaughter and then cryopreserved, the dental root portion is removed and the dental crown portion is cut to obtain a bovine tooth strip. The resultant bovine tooth strip is embedded with an epoxy resin. The embedded bovine tooth is ground using a #600 waterproof abrasive paper while pouring water, thereby exposing enamel or dentin, followed by washing with water and further drying. A double-stick tape with a hole having a diameter of 4 mm is applied on the exposed enamel or dentin thereby defining the adhesion area. The defined adhesion area is subjected to a bonding treatment by a bonding technique specified in Examples or Comparative Examples. A plastic mold (inner diameter of 4 mm, height of 2 mm) is fixed on the surface subjected to the bonding treatment and the mold is filled with a photopolymerizable composite resin (BEAUTIFIL, manufactured by SHOFU INC.). The photopolymerizable composite resin is cured by irradiating with light for 30 seconds using a photopolymerization irradiation machine (Griplight II, manufactured by SHOFU INC.). After curing, the mold is removed and the resultant product is used as a bond test piece. This bond test piece is immersed in distilled water at 37° C. for 24 hours and a dental adhesion test due to a shear adhesive strength is performed at a crosshead speed of 1 mm/min using an Instron universal testing machine (Instron 5567, manufactured by Instron Ltd.).

(2) Durability Test on Dental Substance Adhesion
Evaluation Object:
Evaluation of durability on dental adhesion to enamel and dentin using various dental adhesive primer compositions
Evaluation Procedure:
After making an adhesion test piece in the same manner as in the dental adhesion test, the resultant adhesion test piece is immersed in distilled water at 37° C. for 24 hours. A thermal cycle test of alternately immersing the test piece in a constant temperature water tank maintained at 4° C. and a constant temperature water tank maintained at 60° C. for 1 minute is performed (2,000 cycles). After completion of the thermal cycle test, the adhesion test piece is subjected to a dental adhesion test due to a shear adhesive strength is performed at a crosshead speed of 1 mm/min. using an Instron universal testing machine (Instron 5567, manufactured by Instron Ltd.).

(3) Storage Stability Test
Evaluation Object:
Evaluation of dental adhesion to enamel and dentin using each of composition after storing various dental adhesive primer compositions prepared under an atmosphere at 50° C. for 2 weeks
Evaluation Procedure:
In the same manner as in the dental adhesion test, the dental adhesion test due to the shear adhesive strength is performed.

Abbreviations of materials used in the preparation of the respective dental adhesive primer compositions in Examples and Comparative Examples of the present invention are as follows.

Bis-GMA: 2,2-bis(4-(3-methacryloyloxy-2-hydroxypropoxy)phenyl)propane
UDMA: di(methacryloyloxy)-2,2,4-trimethylhexamethylenediurethane
TGDMA: triethylene glycoldimethacrylate
HEMA: 2-hydroxyethylmethacrylate
CQ: camphorquinone
BPO: benzoyl peroxide
DEPT: N,N-di(β-hydroxyethyl)-p-toluidine
TSN: sodium p-toluenesulfite
DMA: N,N-dimethylaniline
DMB: dimethylaminobenzoic acid
DM: N,N-dimethylaminoethylmethacrylate
MHPA: 6-methacryloyloxyhexylphosphono acetate
MHPP: 6-methacryloyloxyhexyl-3-phosphonopropionate
META: 4-methacryloyloxyethyltrimellitic anhydride
MET: 4-methacryloyloxyethyltrimellitic acid
AETA: 4-acryloyloxyethyltrimellitic anhydride
AET: 4-acryloyloxyethyltrimellitic acid
MEP: 2-methacryloyloxyethyl dihydrogen phosphate
MPP: 5-methacryloyloxypentyl dihydrogen phosphate
MHP: 6-methacryloyloxyhexyl dihydrogen phosphate
MDP: 10-methacryloyloxydecyl dihydrogen phosphate A. Preparation of Primer Compositions

[Preparation of One-Pack Type Primer Compositions (Compositions 1 to 21)]
According to the formulations shown in Table 1, one-pack type primer compositions (compositions 1 to 21) were prepared and used in Examples and Comparative Examples.

TABLE 1

One-pack type primer composition (parts by mass)

| Composition No. | Phosphonic acid group-containing polymerizable monomer | | Polyhydric carboxylic acid group-containing polymerizable monomer | | | | Hydrophobic polymerizable monomer | | | Water | Water-soluble organic solvent | | Polymerization catalyst | | |
|---|---|---|---|---|---|---|---|---|---|---|---|---|---|---|---|
| | MHPA | MHPP | MET | AET | META | AETA | Bis-GMA | UDMA | TEGDMA | | Acetone | Ethanol | CQ | DMA | DMB |
| Composition 1 | 3 | — | — | — | 17 | — | — | — | — | 40 | — | 40 | — | — | 1 |
| Composition 2 | — | 2 | 30 | — | — | — | — | — | — | 30 | 38 | — | 0.5 | 1 | — |
| Composition 3 | 1 | — | — | 10 | — | — | — | — | — | 50 | — | 39 | 0.3 | — | 1 |
| Composition 4 | 2 | — | 18 | — | — | — | 20 | — | — | 20 | 40 | — | 0.5 | 1 | — |
| Composition 5 | — | 3 | — | — | — | 12 | — | 15 | — | 30 | — | 40 | 0.5 | — | 1 |
| Composition 6 | 1 | — | — | 5 | — | — | 9 | — | 5 | 50 | 30 | — | 0.5 | 1 | — |
| Composition 7 | — | — | — | — | 8 | — | 10 | — | — | 37 | — | 45 | 0.3 | — | 1 |
| Composition 8 | — | — | 32 | — | — | — | — | 5 | 5 | 20 | 38 | — | 0.5 | 1 | — |
| Composition 9 | — | — | — | 15 | — | — | — | — | — | 46 | — | 39 | 0.3 | — | 1 |
| Composition 10 | — | 10 | — | — | — | — | — | 12 | — | 38 | — | 40 | 0.5 | — | 1 |
| Composition 11 | — | 30 | — | — | — | — | — | 10 | 3 | 27 | 30 | — | 0.3 | 1 | — |
| Composition 12 | 30 | — | — | — | — | — | — | — | — | 50 | — | 20 | 0.3 | — | 1 |
| Composition 13 | 12 | — | 10 | — | — | — | 18 | — | — | 20 | 40 | — | — | — | — |
| Composition 14 | — | 15 | — | — | — | 12 | — | 13 | — | 30 | — | 30 | — | — | — |
| Composition 15 | 20 | — | — | 5 | — | — | 9 | — | 5 | 30 | 31 | — | — | — | — |
| Composition 16 | — | 20 | 20 | — | 8 | — | 20 | — | — | — | — | 32 | 0.5 | — | 1 |
| Composition 17 | 10 | — | — | 25 | — | — | — | — | 15 | — | 50 | — | 0.5 | 1 | — |
| Composition 18 | — | 30 | — | — | 15 | — | — | — | — | — | — | 55 | 0.3 | — | 1 |
| Composition 19 | — | 10 | — | 25 | — | — | 15 | — | — | 50 | — | — | 0.5 | — | 1 |
| Composition 20 | 10 | — | — | 20 | — | — | — | 7 | 3 | 60 | — | — | 0.5 | 1 | — |
| Composition 21 | 15 | — | — | — | 25 | — | — | — | — | 60 | — | — | 0.3 | — | 1 |

[Preparation of Two-Pack Mixing Type Primer Compositions (Compositions 22 to 27)]

According to the formulations shown in Table 2, two-pack mixing type primer compositions (compositions 22 to 27) were prepared and used in Examples.

TABLE 2

Two-pack mixing type primer composition (parts by mass)

| Composition No. | Primer A | | | | | | | | | | | Primer B | | | | |
|---|---|---|---|---|---|---|---|---|---|---|---|---|---|---|---|---|
| | Phosphonic acid group-containing polymerizable monomer | | Polyhydric carboxylic acid group-containing polymerizable monomer | | | | Hydrophobic polymerizable monomer | | | Water-soluble organic solvent | | Water | Water-soluble organic solvent | | Polymerization catalyst | |
| | MHPA | MHPP | MET | AET | META | AETA | Bis-GMA | UDMA | TEGDMA | Acetone | Ethanol | | Acetone | Ethanol | CQ | TSN |
| Composition 22 | 40 | — | 30 | — | — | — | — | — | — | 30 | — | 80 | 20 | — | 0.5 | 5 |
| Composition 23 | — | 5 | — | — | — | 45 | — | — | — | — | 50 | 60 | — | 40 | 0.5 | 5 |
| Composition 24 | 10 | — | — | 10 | — | — | — | — | — | 80 | — | 50 | 50 | — | 0.5 | 5 |
| Composition 25 | — | 40 | — | — | 20 | — | 10 | — | — | — | 30 | 80 | — | 20 | 0.5 | 5 |
| Composition 26 | 30 | — | 5 | — | — | — | 15 | — | — | 50 | — | 60 | 40 | — | 0.5 | 5 |

TABLE 2-continued

Two-pack mixing type primer composition (parts by mass)

| Composition No. | Primer A | | | | | | | | | | | Primer B | | | |
|---|---|---|---|---|---|---|---|---|---|---|---|---|---|---|---|
| | Phosphonic acid group-containing polymerizable monomer | | Polyhydric carboxylic acid group-containing polymerizable monomer | | | | Hydrophobic polymerizable monomer | | | Water-soluble organic solvent | | Water | Water-soluble organic solvent | | Polymerization catalyst |
| | MHPA | MHPP | MET | AET | META | AETA | Bis-GMA | UDMA | TEGDMA | Acetone | Ethanol | | Acetone | Ethanol | CQ | TSN |
| Composition 27 | — | 10 | — | — | — | 15 | 5 | — | 5 | — | 65 | 50 | — | 50 | 0.5 | 5 |

[Preparation of One-Pack Type Primer Compositions (Compositions 28 to 32)]

According to the formulations shown in Table 3, one-pack type primer compositions (compositions 28 to 32) were prepared and used in Comparative Examples.

TABLE 3

One-pack type primer composition containing phosphate ester group-containing polymerizable monomer (parts by mass)

| Composition No. | Phosphonic acid group-containing polymerizable monomer | | | | Polyhydric carboxylic acid group-containing polymerizable monomer | | Hydrophobic polymerizable monomer | | Water | Water-soluble organic solvent | | Polymerization catalyst | | |
|---|---|---|---|---|---|---|---|---|---|---|---|---|---|---|
| | MDP | MEP | MPP | MHP | META | AETA | UDMA | TEGDMA | | Acetone | Ethanol | CQ | DMA | DMB |
| Composition 28 | 1 | — | — | — | 25 | — | 12 | — | 32 | — | 30 | 0.5 | — | 1 |
| Composition 29 | — | 3 | — | — | 28 | — | 9 | 3 | 27 | 30 | — | 0.5 | 1 | — |
| Composition 30 | — | 20 | — | — | 2 | — | — | — | 38 | 40 | — | 0.3 | 1 | — |
| Composition 31 | — | — | 15 | — | — | 3 | — | — | 45 | — | 37 | 0.3 | — | 1 |
| Composition 32 | — | — | — | 17 | — | 5 | — | — | 50 | 28 | — | 0.3 | 1 | — |

B. Preparation of Bonding Material Compositions

[Preparation of Photopolymerizable One-Pack Type Bonding Material Compositions (Compositions A and B)]

According to the formulations shown in Table 4, photopolymerizable one-pack type bonding material compositions (compositions A and B) were prepared and used in Examples and Comparative Examples.

TABLE 4

Photopolymerizable one-pack type bonding material composition (parts by mass)

| Composition No. | Polymerizable monomer | | | | Photopolymerization catalyst system | |
|---|---|---|---|---|---|---|
| | Bis-GMA | UDMA | TEGDMA | HEMA | CQ | DM |
| Composition A | — | 50 | 30 | 20 | 0.5 | 1.0 |
| Composition B | 50 | — | 10 | 40 | 0.5 | 1.0 |

[Dual-Polymerizable Two-Pack Type Bonding Material Compositions (Compositions C and D)]

According to the formulations shown in Table 5, dual-polymerizable two-pack type bonding material compositions (compositions C and D) were prepared and used in Examples and Comparative Examples.

TABLE 5

Dual-polymerizable two-pack type bonding material composition

| | | Polymerizable monomer | | | | Photopolymerization catalyst system | | (parts by mass) Chemical polymerization catalyst system | |
|---|---|---|---|---|---|---|---|---|---|
| Composition No. | | Bis-GMA | UDMA | TEGDMA | HEMA | CQ | DM | DEPT | BPO |
| Composition C | Bond I | — | 50 | 30 | 20 | 0.5 | 1.0 | 1.0 | — |
| | Bond II | — | 50 | 30 | 20 | 0.5 | 1.0 | — | 1.0 |
| Composition D | Bond I | 50 | — | 10 | 40 | 0.5 | 1.0 | 1.0 | — |
| | Bond II | 50 | — | 10 | 40 | 0.5 | 1.0 | — | 1.0 |

C. Evaluation of Dental Adhesion

Examples 1 to 6

A bonding treatment was performed by a two-step type adhesion system comprising a combination of one-pack type primer compositions 1 to 6 and a photopolymerizable one-pack type bonding material composition A or B (application of primer/standing for 10 seconds/drying/application of bonding material/light irradiation for 10 seconds).

After passing through a filling operation of a photopolymerizable composite resin (BEAUTIFIL, manufactured by SHOFU INC.), a dental adhesion test, a durability test on adhesion and a storage stability test were performed. The results are shown in Table 6.

As is apparent from Table 6, the adhesion system comprising one-pack type primer compositions 1 to 6 have excellent dental adhesion (after immersing in water at 37° C. for 24 hours) to enamel and dentin. It was also found that the adhesion system comprising one-pack type primer compositions 1 to 6 have excellent durability on adhesion since an adhesive strength did not decrease with respect to durability on adhesion after about 2,000 thermal cycles in both enamel and dentin when compared with dental adhesion after immersing in water at 37° C. for 24 hours. Furthermore, the one-pack type primer compositions 1 to 6 did not cause deterioration or change in quality as a result of hydrolysis even when stored at 50° C. for 2 weeks and maintained initial dental adhesion (after immersing in water at 37° C. for 24 hours) and were excellent in storage stability.

Comparative Examples 1 to 3

A bonding treatment was performed by a two-step type adhesion system (application of primer/standing for 10 seconds/drying/application of bonding material/light irradiation for 10 seconds) comprising a combination of one-pack type primer compositions 7 to 9 containing no phosphonic acid group-containing polymerizable monomer and a photopolymerizable one-pack type bonding material composition A or B, and the same tests as those in Examples 1 to 6 were performed. The results are shown in Table 6.

As is apparent from Table 6, an adhesion system using one-pack type primer compositions 7 to 9 containing no phosphonic acid group-containing polymerizable monomer shows that the adhesive strength to enamel is lower than that to dentin in any of dental adhesion, durability on adhesion and storage stability.

Comparative Examples 4 to 6

A bonding treatment was performed by a two-step type adhesion system comprising a combination of one-pack type primer compositions 10 to 12 containing no polyhydric carboxylic acid group-containing polymerizable monomer and a photopolymerizable one-pack type bonding material composition A or B (application of primer/standing for 10 seconds/drying/application of bonding material/light irradiation for 10 seconds) and the same tests as in Examples 1 to 6 were performed. The results are shown in Table 6.

As is apparent from Table 6, an adhesion system using one-pack type primer compositions 10 to 12 containing no polyhydric carboxylic acid group-containing polymerizable monomer shows that the adhesive strength of dentin is lower than that of enamel in any of dental adhesion, durability on adhesion and storage stability.

Comparative Examples 7 to 9

A bonding treatment was performed using a two-step type adhesion system comprising a combination of one-pack type primer compositions 13 to 15 containing no polymerization catalyst and a photopolymerizable one-pack type bonding material composition A or B (application of primer/standing for 10 seconds/drying/application of bonding material/light irradiation for 10 seconds) and the same tests as in Examples 1 to 6 were performed. The results are shown in Table 6.

As is apparent from Table 6, an adhesion system using one-pack type primer compositions 13 to 15 containing no polymerization catalyst shows that adhesion to dentin is lower than that to enamel in dental adhesion and durability on adhesion. It was also found that adhesion to both enamel and dentin are low in storage stability.

Comparative Examples 10 to 12

A bonding treatment was performed by a two-step type adhesion system comprising a combination of one-pack type primer composition 16 to 18 containing no water and a photopolymerizable one-pack type bonding material composition A or B (application of primer/standing for 10 seconds/drying/application of bonding material/light irradiation for 10 seconds) and the same tests as in Examples 1 to 6 were performed. The results are shown in Table 6.

As is apparent from Table 6, an adhesion system using one-pack type primer compositions 16 to 18 containing no water shows no adhesion to both of enamel and dentin in any of dental adhesion, durability on adhesion and storage stability.

Comparative Examples 13 to 15

A bonding treatment was performed by a two-step type adhesion system comprising a combination of one-pack type primer compositions 19 to 21 containing no water-soluble organic solvent and a photopolymerizable one-pack type bonding material composition A or B (application of primer/standing for 10 seconds/drying/application of bonding material/light irradiation for 10 seconds) and the same tests as in Example 1 to 6 were performed. The results are shown in Table 6.

Any of one-pack type primer compositions 19 to 21 containing no water-soluble organic solvent were in a heterogeneous state.

As is apparent from Table 6, an adhesion system using one-pack type primer compositions 19 to 21 containing no water showed stable adhesion to both of enamel and dentin in dental adhesion and durability on adhesion regardless of comparatively low. However, it was found that adhesion to enamel was drastically lower than that to dentin in storage stability.

Examples 7 to 12

A bonding treatment was performed by a two-step type adhesion system comprising a combination of a dual-polymerizable two-pack type bonding material composition C or D and one-pack type primer compositions 1 to 6 (application of primer/standing for 10 seconds/drying/mixing of bonding materials in the same amount and application). After passing through a filling operation of a photopolymerizable composite resin (BEAUTIFIL, manufactured by SHOFU INC.), a dental adhesion test, a durability test on dental adhesion and a storage stability test were performed. The results are shown in Table 6.

As is apparent from Table 6, one-pack type primer compositions 1 to 6 have excellent dental adhesion (after immersing in water at 37° C. for 24 hours) to enamel and dentin even in an adhesion system comprising a dual-polymerizable bonding material. It was also found that one-pack type primer compositions have excellent durability on adhesion since the adhesive strength with respect to durability on adhesion after 2,000 thermal cycles of both enamel and dentin does not decrease when compared with dental adhesion after immersing in water at 37° C. for 24 hours. Furthermore, the one-pack type primer compositions 1 to 6 did not cause deterioration or change in quality as a result of hydrolysis even when stored at 50° C. for 2 weeks and maintained initial dental adhesion (after immersing in water at 37° C. for 24 hours) and were excellent in storage stability.

Examples 13 to 18

A bonding treatment was performed by a one-step adhesion system using a one-pack type primer compositions 1 to 6 alone (application of primer/standing for 10 seconds/drying/light irradiation for 10 seconds) and the same tests as in Examples 1 to 6 were performed. The results are shown in Table 6.

As is apparent from Table 6, an adhesion system using one-pack type primer compositions 1 to 6 alone shows that adhesion to both of enamel and dentin is stable in any of dental adhesion, durability on adhesion and storage stability regardless of a low level when compared with an adhesion system using a photopolymerizable one-pack type and a dual-polymerizable two-pack type bonding material in combination.

TABLE 6

Results of adhesion system comprising one-pack type primer composition in various tests

| Example No. | Primer composition No. | Bonding material composition No. | Dental Adhesion (after immersion in water at 37° C. for 24 hr) (MPa) | | Durability on Adhesion (after immersion in water at 37° C. for 24 hr → after 2,000 thermal cycles) (MPa) | | Storage stability (product stored at 50° C. for 2 weeks → after immersion in water at 37° C. for 24 hr) (Mpa) | |
|---|---|---|---|---|---|---|---|---|
| | | | Enamel | Dentin | Enamel | Dentin | Enamel | Dentin |
| Example 1 | Composition 1 | One-pack type composition A | 17.2 | 16.9 | 17.5 | 18.4 | 14.9 | 18.2 |
| Example 2 | Composition 2 | One-pack type composition B | 18.3 | 17.2 | 18.5 | 16.9 | 15.8 | 18.2 |
| Example 3 | Composition 3 | One-pack type composition A | 17.9 | 18.2 | 18.2 | 18.7 | 15.1 | 18.7 |
| Example 4 | Composition 4 | One-pack type composition A | 20.1 | 21.2 | 17.4 | 21.5 | 15.9 | 20.1 |
| Example 5 | Composition 5 | One-pack type composition B | 18.2 | 21.5 | 18.3 | 21.1 | 17.5 | 19.8 |
| Example 6 | Composition 6 | One-pack type composition A | 19.2 | 20.5 | 18.8 | 21.3 | 15.2 | 20.3 |
| Example 7 | Composition 1 | Two-pack mixing type composition C | 17.8 | 18.1 | 16.9 | 18.5 | 14.7 | 18.1 |
| Example 8 | Composition 2 | Two-pack mixing type composition D | 18.1 | 18.1 | 17.7 | 18.8 | 17.2 | 17.9 |

TABLE 6-continued

Results of adhesion system comprising one-pack type primer composition in various tests

| Example No. | Primer composition No. | Bonding material composition No. | Dental Adhesion (after immersion in water at 37° C. for 24 hr) (MPa) | | Durability on Adhesion (after immersion in water at 37° C. for 24 hr → after 2,000 thermal cycles) (MPa) | | Storage stability (product stored at 50° C. for 2 weeks → after immersion in water at 37° C. for 24 hr) (Mpa) | |
|---|---|---|---|---|---|---|---|---|
| | | | Enamel | Dentin | Enamel | Dentin | Enamel | Dentin |
| Example 9 | Composition 3 | Two-pack mixing type composition C | 17.8 | 17.4 | 17.7 | 17.4 | 16.1 | 17.7 |
| Example 10 | Composition 4 | Two-pack mixing type composition C | 19.5 | 20.4 | 21.3 | 21.7 | 16.5 | 20.3 |
| Example 11 | Composition 5 | Two-pack mixing type composition D | 20.1 | 21.1 | 19.2 | 20.3 | 15.4 | 19.9 |
| Example 12 | Composition 6 | Two-pack mixing type composition C | 20.1 | 20.7 | 19.2 | 21.3 | 16.7 | 20.1 |
| Example 13 | Composition 1 | — | 13.2 | 13.4 | 14.1 | 12.9 | 13.1 | 13.1 |
| Example 14 | Composition 2 | — | 14.9 | 15.8 | 14.8 | 14.1 | 14.1 | 15.6 |
| Example 15 | Composition 3 | — | 14.2 | 15.8 | 14.3 | 14.9 | 13.9 | 14.1 |
| Example 16 | Composition 4 | — | 13.3 | 15.5 | 13.9 | 16.7 | 13.8 | 15.5 |
| Example 17 | Composition 5 | — | 14.5 | 16.1 | 14.2 | 16.4 | 14.7 | 14.8 |
| Example 18 | Composition 6 | — | 14.7 | 16.1 | 15.1 | 15.2 | 13.2 | 14.2 |
| Comparative Example 1 | Composition 7 | Composition A | 12.1 | 19.2 | 12.6 | 19.5 | 11.2 | 18.9 |
| Comparative Example 2 | Composition 8 | Composition B | 11.5 | 18.7 | 11.9 | 18.7 | 10.5 | 17 |
| Comparative Example 3 | Composition 9 | Composition A | 11.9 | 16.5 | 12.3 | 17.4 | 10.9 | 18.4 |
| Comparative Example 4 | Composition 10 | Composition B | 18.2 | 9.2 | 18.5 | 9.8 | 15.6 | 6.9 |
| Comparative Example 5 | Composition 11 | Composition A | 17.9 | 10.7 | 17.4 | 9.6 | 15.4 | 7.2 |
| Comparative Example 6 | Composition 12 | Composition B | 17.5 | 9.9 | 18.4 | 9.7 | 14.2 | 7.2 |
| Comparative Example 7 | Composition 13 | Composition A | 15.2 | 9.2 | 14.3 | 8.8 | 10.2 | 8.8 |
| Comparative Example 8 | Composition 14 | Composition B | 14.2 | 8.8 | 13.9 | 9.1 | 9.5 | 9.2 |
| Comparative Example 9 | Composition 15 | Composition A | 14.8 | 8.9 | 14.1 | 7.6 | 11.2 | 9.1 |
| Comparative Example 10 | Composition 16 | Composition B | 0 | 5.4 | 0 | 0 | 0 | 6.7 |
| Comparative Example 11 | Composition 17 | Composition A | 0 | 5.2 | 0 | 0 | 0 | 5.2 |
| Comparative Example 12 | Composition 18 | Composition B | 0 | 6.1 | 0 | 0 | 0 | 6.6 |
| Comparative Example 13 | Composition 19 | Composition A | 15.4 | 15.1 | 14.7 | 15.9 | 10.5 | 15.9 |
| Comparative Example 14 | Composition 20 | Composition B | 15.4 | 14.9 | 16.1 | 13.9 | 11.2 | 14.2 |
| Comparative Example 15 | Composition 21 | Composition A | 12.3 | 15.1 | 16.3 | 13.9 | 10.5 | 13.4 |

Examples 19 to 24

A bonding treatment was performed by a two-step type adhesion system comprising a combination of two-pack mixing type primer compositions 22 to 27 prepared above and a photopolymerizable one-pack type bonding material composition A or B (mixing of primers in the same amount and application/standing for 10 seconds/drying/application of bonding material/light irradiation for 10 seconds).

After passing through a filling operation of a photopolymerizable composite resin (BEAUTIFUL, manufactured by SHOFU INC.), a dental adhesion test, a durability test on dental adhesion and a storage stability test were performed. The results are shown in Table 7.

As is apparent from Table 7, an adhesion system comprising two-pack mixing type primer compositions 22 to 27 and a photopolymerizable bonding material composition has excellent dental adhesion (after immersing in water at 37° C. for 24 hours) to enamel and dentin. It was also found that two-pack mixing type primer compositions have excellent durability on adhesion since the adhesive strength with respect to durability on adhesion after 2,000 thermal cycles for both enamel and dentin did not decrease when compared with dental adhesion after immersing in water at 37° C. for 24 hours. Furthermore, two-pack mixing type primer compositions 22 to 27 did not cause deterioration or change in quality as a result of hydrolysis even when stored at 50° C. for 2 weeks and maintained initial dental adhesion (after immersing in water at 37° C. for 24 hours) and were excellent in storage stability.

Examples 25 to 30

A bonding treatment was performed by a two-step type adhesion system comprising a combination of the two-pack mixing type primer compositions 22 to 27 used in Examples 19 to 24 and a dual-polymerizable two-pack type bonding material composition C or D (mixing of primers in the same amount and application/standing for 10 seconds/drying/mixing of bonding materials in the same amount and application/light irradiation for 10 seconds) and the same tests as in Examples 19 to 24 were performed. The results are shown in Table 7.

As is apparent from Table 7, an adhesion system comprising two-pack mixing type primer compositions 22 to 27 and a photopolymerizable bonding material composition has excellent dental adhesion (after immersing in water at 37° C. for 24 hours) to enamel and dentin. It was also found that two-pack mixing type primer compositions have excellent durability on adhesion since the adhesive strength with respect to durability on adhesion after 2,000 thermal cycles of both enamel and dentin did not decrease when compared with dental adhesion after immersing in water at 37° C. for 24 hours. Furthermore, two-pack mixing type primer compositions 22 to 27 did not cause deterioration or change in quality as a result of hydrolysis even when stored at 50° C. for 2 weeks and maintained initial dental adhesion (after immersing in water at 37° C. for 24 hours) and were excellent in storage stability.

Examples 31 to 36

A bonding treatment was performed by a one-step adhesion system using two-pack mixing type primer compositions 22 to 27 used in Examples 19 to 24 alone (mixing of primers in the same amount and application/standing for 10 seconds/drying/light irradiation for 10 seconds) and the same tests as in Examples 19 to 24 were performed. The results are shown in Table 7.

As is apparent from Table 7, an adhesion system using two-pack mixing type primer compositions 22 to 27 alone shows that adhesion to both of enamel and dentin is stable in any of dental adhesion, durability on adhesion and storage stability regardless of a low level when compared with an adhesion system using a photopolymerizable one-pack type and a dual-polymerizable two-pack type bonding material in combination.

TABLE 7

Results of adhesion system comprising two-pack type primer composition in various tests

| Example No. | Primer composition No. | Bonding material composition No. | Dental Adhesion Enamel | Dental Adhesion Dentin | Durability on Adhesion Enamel | Durability on Adhesion Dentin | Storage stability Enamel | Storage stability Dentin |
|---|---|---|---|---|---|---|---|---|
| Example 19 | Composition 22 | One-pack type composition A | 18.1 | 17.4 | 18.2 | 17.9 | 15.9 | 18.4 |
| Example 20 | Composition 23 | One-pack type composition B | 17.2 | 17.2 | 18.8 | 17.8 | 15.7 | 18.4 |
| Example 21 | Composition 24 | One-pack type composition A | 18.5 | 16.9 | 17.4 | 17.6 | 16.5 | 18.1 |
| Example 22 | Composition 25 | One-pack type composition B | 18.9 | 21.2 | 17.3 | 20.9 | 15.7 | 21.2 |
| Example 23 | Composition 26 | One-pack type composition A | 18.2 | 20.9 | 19 | 20.5 | 15.2 | 20.4 |
| Example 24 | Composition 27 | One-pack type composition B | 17.9 | 21.3 | 18.7 | 20.7 | 16.2 | 20.4 |

| Example No. | Primer composition No. | Bonding material composition No. | Dental Adhesion Enamel | Dental Adhesion Dentin | Durability on Adhesion Enamel | Durability on Adhesion Enamel | Storage stability Dentin | Storage stability Enamel |
|---|---|---|---|---|---|---|---|---|
| Example 25 | Composition 22 | Two-pack mixing type composition C | 16.9 | 16.5 | 17.1 | 18.9 | 17.2 | 17.9 |
| Example 26 | Composition 23 | Two-pack mixing type composition D | 18.9 | 19.2 | 17.1 | 19.9 | 16.7 | 18.5 |
| Example 27 | Composition 24 | Two-pack mixing type composition C | 18.2 | 18.2 | 16.9 | 17.5 | 16.7 | 18.5 |

TABLE 7-continued

Results of adhesion system comprising two-pack type primer composition in various tests

| Example 28 | Composition 25 | Two-pack mixing type composition D | 18.6 | 20.5 | 17.8 | 19.9 | 16.5 | 20.4 |
|---|---|---|---|---|---|---|---|---|
| Example 29 | Composition 26 | Two-pack mixing type composition C | 17.6 | 21.2 | 18.2 | 20.4 | 17.8 | 20.4 |
| Example 30 | Composition 27 | Two-pack mixing type composition D | 18.9 | 21.2 | 19.2 | 21.5 | 17.8 | 20.9 |
| Example 31 | Composition 22 | — | 14 | 14.5 | 15.1 | 15.2 | 14.1 | 15.1 |
| Example 32 | Composition 23 | — | 13.8 | 14.7 | 14.5 | 14.1 | 13.9 | 15.1 |
| Example 33 | Composition 24 | — | 14.1 | 15.7 | 15.2 | 14.5 | 13.9 | 14.7 |
| Example 34 | Composition 25 | — | 14.5 | 18.9 | 14.9 | 19.2 | 14.8 | 19.9 |
| Example 35 | Composition 26 | — | 15.9 | 20.3 | 13.9 | 19.4 | 14.9 | 18.7 |
| Example 36 | Composition 27 | — | 14.7 | 18.2 | 13.9 | 18.7 | 14.7 | 19.2 |

Comparative Examples 16 to 20

A bonding treatment was performed by a two-step type adhesion system comprising a combination of one-pack type primer compositions 28 to 32 prepared by using a polymerizable monomer having a phosphate ester group in the molecule in place of the phosphonic acid group-containing polymerizable monomer and a photopolymerizable one-pack type bonding material composition A or B (Comparative Example 16 to 20: application of primer/standing for 10 seconds/drying/application of bonding material/light irradiation for 10 seconds) and the same tests as in Examples 1 to 6 were performed. The results are shown in Table 8.

As is apparent from Table 8, when one-pack type primer compositions 28 and 29 containing a hydrophobic polymerizable monomer mixed therein are used, since each one-pack type primer composition causes deterioration or change in quality as a result of hydrolysis in storage stability when stored at 50° C. for 2 weeks, adhesion to enamel is lower than that to dentin.

It was also found that adhesion drastically decreases when compared with adhesion (after immersing in water at 37° C. for 24 hours) to enamel at an initial stage. It was also found that, when one-pack type primer compositions 30 to 32 containing no hydrophobic polymerizable monomer are used, adhesion to dentin is lower than that to enamel in any of dental adhesion, durability on adhesion and storage stability. It was also found that adhesion to dentin is drastically low in storage stability and drastically decreases when compared with adhesion (after immersing in water at 37° C. for 24 hours) to dentin at an initial stage.

Comparative Examples 21 to 25

A bonding treatment was performed by one-step adhesion system using one-pack type primer compositions 28 to 32 alone application of primer/standing for 10 seconds/drying/light irradiation for 10 seconds) and the same tests as in Examples 1 to 6 were performed. The results are shown in Table 8.

As is apparent from Table 8, when one-pack type primer compositions 28 and 29 containing a hydrophobic polymerizable monomer mixed therein are used, since each one-pack type primer composition causes deterioration or change in quality as a result of hydrolysis in storage stability when stored at 50° C. for 2 weeks, adhesion to enamel is lower than that to dentin. It was also found that adhesion drastically decreases when compared with adhesion (after immersing in water at 37° C. for 24 hours) to enamel at an initial stage. It was also found that, when one-pack type primer compositions 30 to 32 containing no hydrophobic polymerizable monomer are used, adhesion to dentin is lower than that to enamel in any of dental adhesion, durability on adhesion and storage stability. It was also found that adhesion to dentin is drastically low in storage stability and drastically decreases when compared with adhesion (after immersing in water at 37° C. for 24 hours) to dentin at an initial stage.

TABLE 8

Results of adhesion system comprising one-pack type primer composition containing phosphate ester group-containing polymerizable monomer in various tests

| | Primer composition | Bonding material composition | Dental Adhesion (after immersion in water at 37° C. for 24 hr) (MPa) | | Durability on Adhesion (after immersion in water at 37° C. for 24 hr → after 2,000 thermal cycles) (Mpa) | | Storage stability (product stored at 50° C. for 2 weeks → after immersion in water at 37° C. for 24 hr) (MPa) | |
|---|---|---|---|---|---|---|---|---|
| Example No. | No. | No. | Enamel | Dentin | Enamel | Dentin | Enamel | Dentin |
| Comparative Example 16 | Composition 28 | One-pack type composition B | 17.1 | 20.2 | 17.2 | 18.4 | 9.2 | 17.4 |

TABLE 8-continued

Results of adhesion system comprising one-pack type primer composition containing phosphate ester group-containing polymerizable monomer in various tests

| Example No. | Primer composition No. | Bonding material composition No. | Dental Adhesion (after immersion in water at 37° C. for 24 hr) (MPa) Enamel | Dentin | Durability on Adhesion (after immersion in water at 37° C. for 24 hr → after 2,000 thermal cycles) (Mpa) Enamel | Dentin | Storage stability (product stored at 50° C. for 2 weeks → after immersion in water at 37° C. for 24 hr) (MPa) Enamel | Dentin |
|---|---|---|---|---|---|---|---|---|
| Comparative Example 17 | Composition 29 | One-pack type composition A | 16.9 | 19.2 | 17.2 | 18.4 | 9.9 | 16.9 |
| Comparative Example 18 | Composition 30 | One-pack type composition A | 17.2 | 12.5 | 16.9 | 12.7 | 14.4 | 7.4 |
| Comparative Example 19 | Composition 31 | One-pack type composition B | 18.5 | 14.3 | 18.4 | 12.9 | 13.9 | 7.4 |
| Comparative Example 20 | Composition 32 | One-pack type composition A | 16.7 | 13.8 | 16.7 | 13.7 | 14.2 | 6.2 |
| Comparative Example 21 | Composition 28 | — | 15.4 | 15.9 | 14.3 | 16.9 | 8.1 | 15.4 |
| Comparative Example 22 | Composition 29 | — | 14.2 | 16.1 | 15.9 | 15.1 | 8.2 | 14.3 |
| Comparative Example 23 | Composition 30 | — | 14.2 | 12.1 | 14.3 | 11.5 | 12.1 | 5.9 |
| Comparative Example 24 | Composition 31 | — | 13.8 | 11.9 | 13.9 | 11.9 | 12.1 | 6.7 |
| Comparative Example 25 | Composition 32 | — | 13.9 | 12.3 | 13.7 | 12.3 | 11.9 | 5.3 |

The invention claimed is:

1. A dental adhesive primer composition in a homogenous state consisting of:
   (a) 0.1 to 40 parts by weight of a phosphonic acid group-containing polymerizable monomer, which is represented by the following formula (I),

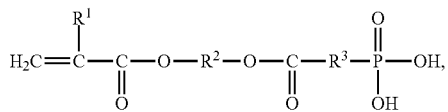

wherein $R^1$ represents a hydrogen atom or a methyl group, $R^2$ represents an alkylene group having 5 to 10 carbon atoms, and $R^3$ represents an alkylene group having 1 to 6 carbon atoms;
   (b) 0.1 to 40 parts by weight of a polyhydric carboxylic acid group-containing polymerizable monomer;
   (c) 0.1 to 50 parts by weight of water;
   (d) 24.3 to 56.0 parts by weight of a water-soluble organic solvent; and
   (e) 0.1 to 15 parts by weight of a polymerization catalyst.

2. A dental adhesive primer composition in a homogenous state consisting of:
   (a) 0.1 to 40 parts by weight of a phosphonic acid group-containing polymerizable monomer, which is represented by the following formula (I),

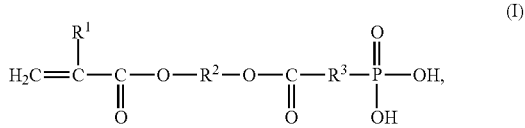

wherein $R^1$ represents a hydrogen atom or a methyl group, $R^2$ represents an alkylene group having 5 to 10 carbon atoms, and $R^3$ represents an alkylene group having 1 to 6 carbon atoms;
   (b) 0.1 to 40 parts by weight of a polyhydric carboxylic acid group-containing polymerizable monomer;
   (c) 0.1 to 50 parts by weight of water;
   (d) 24.3 to 56.0 parts by weight of a water-soluble organic solvent;
   (e) 0.1 to 15 parts by weight of at least one polymerization catalyst; and
   (f) 4.9 to 19.7 parts by weight of a hydrophobic polymerizable monomer selected from the group consisting of:
      (i) 2,2-bis(4-(3-methacryloyloxy-2-hydroxypropoxy)phenyl)propane (Bis-GMA),
      (ii) 2,2-bis(4-methacryloyloxyethoxyphenyl)propane (D-2.6E),
      (iii) di(methacryloyloxy)-2,2,4-trimethylhexamethylenediurethane (UDMA),
      (iv) triethylene glycol dimethacrylate (TEGDMA),
      (v) neopentyl glycol dimethacrylate, and
      (vi) trimethylolpropane trimethacrylate.

* * * * *